(12) United States Patent
Lovchinsky et al.

(10) Patent No.: US 11,715,211 B2
(45) Date of Patent: Aug. 1, 2023

(54) METHODS AND APPARATUSES FOR ANALYZING IMAGING DATA

(71) Applicant: BFLY Operations, Inc., Guilford, CT (US)

(72) Inventors: Igor Lovchinsky, New York, NY (US); Nathan Silberman, Brooklyn, NY (US)

(73) Assignee: BFLY OPERATIONS, INC., Burlington, MA (US)

( * ) Notice: Subject to any disclaimer, the term of this patent is extended or adjusted under 35 U.S.C. 154(b) by 81 days.

(21) Appl. No.: 16/880,272

(22) Filed: May 21, 2020

(65) Prior Publication Data

US 2020/0372657 A1 Nov. 26, 2020

Related U.S. Application Data

(60) Provisional application No. 62/851,502, filed on May 22, 2019.

(51) Int. Cl.
*G06T 7/143* (2017.01)
*G06T 7/00* (2017.01)
*G06T 7/11* (2017.01)

(52) U.S. Cl.
CPC ............ *G06T 7/143* (2017.01); *G06T 7/0012* (2013.01); *G06T 7/11* (2017.01); *G06T 2207/10132* (2013.01); *G06T 2207/30204* (2013.01)

(58) Field of Classification Search
None
See application file for complete search history.

(56) References Cited

U.S. PATENT DOCUMENTS

| | | | | |
|---|---|---|---|---|
| 7,458,936 | B2 * | 12/2008 | Zhou | G16H 50/20 600/407 |
| 7,599,534 | B2 * | 10/2009 | Krishnan | G06T 7/0012 382/128 |
| 9,792,681 | B2 * | 10/2017 | Bryan | G06V 10/42 |
| 10,231,704 | B2 * | 3/2019 | Raghavan | G16H 30/00 |
| 10,510,449 | B1 | 12/2019 | Reicher et al. | |
| 10,628,932 | B2 | 4/2020 | Rothberg et al. | |

(Continued)

FOREIGN PATENT DOCUMENTS

| | | | | |
|---|---|---|---|---|
| EP | 3379488 A1 * | 9/2018 | | A61B 5/7425 |
| WO | WO 2015/087218 A1 | 6/2015 | | |
| WO | WO-2017222970 A1 * | 12/2017 | | A61B 8/02 |

OTHER PUBLICATIONS

International Search Report and Written Opinion dated Aug. 17, 2020 in connection with International Application No. PCT/US2020/033949.

(Continued)

*Primary Examiner* — Vu Le
*Assistant Examiner* — Courtney Joan Nelson
(74) *Attorney, Agent, or Firm* — Osha Bergman Watanabe & Burton LLP

(57) ABSTRACT

Aspects of the technology described herein relate to automatically calculating and displaying a prediction of a collective opinion of a group of individuals regarding imaging data and/or an output based on the imaging data. In some embodiments, the prediction may be a prediction of the collective opinion of a group of individuals regarding the usability of imaging data, regarding a segmentation of an image, or regarding a measurement performed based on the imaging data.

19 Claims, 9 Drawing Sheets

(56) References Cited

U.S. PATENT DOCUMENTS

| | | |
|---|---|---|
| 2011/0055447 A1 | 3/2011 | Costa |
| 2014/0276162 A1 | 9/2014 | Albert et al. |
| 2015/0235242 A1* | 8/2015 | Labriola ............... G06Q 40/06 705/7.32 |
| 2016/0048934 A1 | 2/2016 | Gross |
| 2017/0360397 A1 | 12/2017 | Rothberg et al. |
| 2017/0360401 A1 | 12/2017 | Rothberg et al. |
| 2017/0360403 A1 | 12/2017 | Rothberg et al. |
| 2018/0060512 A1* | 3/2018 | Sorenson ............... G06T 7/0012 |
| 2019/0130554 A1 | 5/2019 | Rothberg et al. |
| 2019/0142388 A1 | 5/2019 | Gonyeau et al. |
| 2019/0196600 A1 | 6/2019 | Rothberg et al. |
| 2019/0266716 A1 | 8/2019 | Rothberg et al. |
| 2019/0282208 A1 | 9/2019 | Silberman et al. |
| 2019/0307428 A1 | 10/2019 | Silberman et al. |
| 2020/0037986 A1 | 2/2020 | Silberman et al. |
| 2020/0037987 A1 | 2/2020 | Silberman et al. |
| 2020/0037998 A1 | 2/2020 | Gafner et al. |
| 2020/0046322 A1 | 2/2020 | Silberman |
| 2020/0054307 A1 | 2/2020 | Silberman et al. |
| 2020/0060658 A1 | 2/2020 | Gafner et al. |

OTHER PUBLICATIONS

Foncubierta-Rodríguez et al., Ground Truth Generation in Medical Imaging—A Crowdsourcing-based Iterative Approach, CrowdMM'12, Oct. 29, 2012; 9-14.

Romanowski et al., X-ray Imaging Analysis of Silo Flow Parameters Based on Trace Particles Using Targeted Crowdsourcing. Institute of Applied Computer Science. Lodz University of Technology, Sensors. Jul. 28, 2019; 19(3317):18 pages.

International Preliminary Report on Patentability for International Application No. PCT/US2020/033949, dated Dec. 2, 2021.

Woudenberg, N.V et al., "Quantitative Echocardiography: Real-Time Quality Estimation and View Classification Implemented on a Mobile Android Device," SAT 2015 18th International Conference, Austin, TX, USA, Sep. 24-27, 2015 (8 pages).

Tanno, R. et al., "Learning from Noisy Labels by Regularized Estimation of Annotator Confusion," ARXIV.org, Cornell University Library, 201 Olin Library Cornell University Itchaca, NY, 14853, XP081027477, Feb. 11, 2019 (13 pages).

Extended European Search Report issued in corresponding European Application No. 20810125.3; dated May 16, 2023 (10 pages).

* cited by examiner

METHODS AND APPARATUSES FOR ANALYZING IMAGING DATA

CROSS-REFERENCE TO RELATED APPLICATIONS

This application claims the benefit under 35 U.S.C. § 119(e) of U.S. Provisional Application Ser. No. 62/851,502, filed on May 22, 2019and entitled "METHODS AND APPARATUSES FOR ANALYZING IMAGING DATA," which is hereby incorporated by reference herein in its entirety.

FIELD

Generally, the aspects of the technology described herein relate to analyzing imaging data. Some aspects relate to methods and apparatuses for calculating and displaying a prediction of the collective opinion of a group of individuals regarding imaging data and/or outputs based on imaging data.

BACKGROUND

Medical imaging may be used to perform diagnosing imaging and/or treatment. For example, ultrasound imaging may be used to see internal soft tissue body using sound waves with frequencies that are higher than those audible to humans. When pulses of ultrasound are transmitted into tissue, sound waves of different amplitudes may be reflected back towards the probe at different tissue interfaces. These reflected sound waves may then be recorded and displayed as an image to the operator. The strength (amplitude) of the sound signal and the time it takes for the wave to travel through the body may provide information used to produce the ultrasound image.

SUMMARY

According to one aspect, an apparatus comprises processing circuitry configured to automatically calculate a prediction of a collective opinion of a group of individuals regarding imaging data and/or an output based on the imaging data and display the prediction of the collective opinion of the group of individuals regarding the imaging data and/or the output based on the imaging data.

In some embodiments, the processing circuitry is configured, when automatically calculating the collective opinion of the group of individuals regarding the imaging data and/or the output based on the imaging data, to calculate a prediction of a collective opinion of a group of individuals regarding usability of imaging data. In some embodiments, the processing circuitry is configured, when automatically calculating the collective opinion of the group of individuals regarding the imaging data and/or the output based on the imaging data, to calculate a prediction of a fraction of the group of individuals who would classify the imaging data as clinically usable. In some embodiments, the processing circuitry is configured, when displaying the prediction of the collective opinion of the group of individuals regarding the imaging data and/or the output based on the imaging data, to display the fraction. In some embodiments, the processing circuitry is configured, when displaying the prediction of the collective opinion of the group of individuals regarding the imaging data and/or the output based on the imaging data, to display a frame having a first end and a second end and a marker within the frame, such that a distance from the first end of the frame to the marker divided by the distance from the first end to the second of the marker is approximately equal to the fraction.

In some embodiments, the processing circuitry is configured, when automatically calculating the prediction of the collective opinion of the group of individuals regarding the imaging data and/or the output based on the imaging data, to calculate a prediction of a collective opinion of a group of individuals regarding a segmentation of the imaging data. In some embodiments, the processing circuitry is configured, when automatically calculating the prediction of the collective opinion of the group of individuals regarding the imaging data and/or the output based on the imaging data, to calculate a prediction of a fraction of the group of individuals who would agree that a segmentation automatically performed based on one or more images was performed correctly. In some embodiments, the processing circuitry is configured, when displaying the prediction of the collective opinion of the group of individuals regarding the imaging data and/or the output based on the imaging data, to display the fraction. In some embodiments, the processing circuitry is configured, when displaying the prediction of the collective opinion of the group of individuals regarding the imaging data and/or the output based on the imaging data, to display a frame having a first end and a second end and a marker within the frame, such that a distance from the first end of the frame to the marker divided by the distance from the first end to the second of the marker is approximately equal to the fraction. In some embodiments, the processing circuitry is configured, when automatically calculating the prediction of the collective opinion of the group of individuals regarding the imaging data and/or the output based on the imaging data, to calculate a prediction of the fraction of a group of individuals who would believe that a given pixel in an image is within a segmented region. In some embodiments, the processing circuitry is configured, when automatically calculating the prediction of the collective opinion of the group of individuals regarding the imaging data and/or the output based on the imaging data, to generate a segmentation mask where a value of a property of each pixel in the segmentation mask is proportional to a prediction of a fraction of the group of individuals who would believe that a corresponding pixel in an image is inside a segmented region. In some embodiments, the processing circuitry is configured, when displaying the prediction of the collective opinion of the group of individuals regarding the imaging data and/or the output based on the imaging data, to display the segmentation mask. In some embodiments, the processing circuitry is configured to overlay the segmentation mask on the image.

In some embodiments, the processing circuitry is configured, when automatically calculating the prediction of the collective opinion of the group of individuals regarding the imaging data and/or the output based on the imaging data, to calculate a prediction of a collective opinion of a group of individuals regarding a measurement performed based on the imaging data. In some embodiments, the processing circuitry is configured, when automatically calculating the prediction of the collective opinion of the group of individuals regarding the imaging data and/or the output based on the imaging data, to calculate a prediction of a distribution of measurement values that would be manually calculated based on the imaging data by the group of individuals. In some embodiments, the processing circuitry is configured, when displaying the prediction of the collective opinion of the group of individuals regarding the imaging data and/or the output based on the imaging data, to graphically display the distribution. In some embodiments, the processing circuitry is configured, when automatically calculating the prediction of the collective opinion of the group of individuals regarding the imaging data and/or the output based on the imaging data, to calculate a prediction of an approximation of a distribution of measurement values that would be manually calculated based on the imaging data by the group of individuals. In some embodiments, the approximation comprises a mean, a standard deviation, a confidence interval, and/or a percentile. In some embodiments, the processing circuitry is configured, when displaying the prediction of the collective opinion of the group of individuals regarding the imaging data and/or the output based on the imaging data, to display the approximation.

In some embodiments, the processing circuitry is configured to automatically calculate the prediction of the collective opinion of the group of individuals regarding imaging data and/or the output based on the imaging data using a statistical model. In some embodiments, the processing circuitry is configured to automatically calculate and display the prediction of the collective opinion of the group of individuals regarding the imaging data and/or the output based on the imaging data as the imaging data is collected. In some embodiments, the processing circuitry is configured to receive the imaging data. In some embodiments, the processing circuitry is configured to receive the imaging data from an imaging device. In some embodiments, the processing circuitry is in operative communication with an imaging device that collected the imaging data. In some embodiments, the imaging data comprises ultrasound data.

Some aspects include a method to perform the actions that the apparatus is configured to perform. Some aspects include at least one non-transitory computer-readable storage medium storing processor-executable instructions that, when executed by at least one processor, cause the at least one processor to perform the actions that the apparatus is configured to perform.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

DETAILED DESCRIPTION

Figure 1:
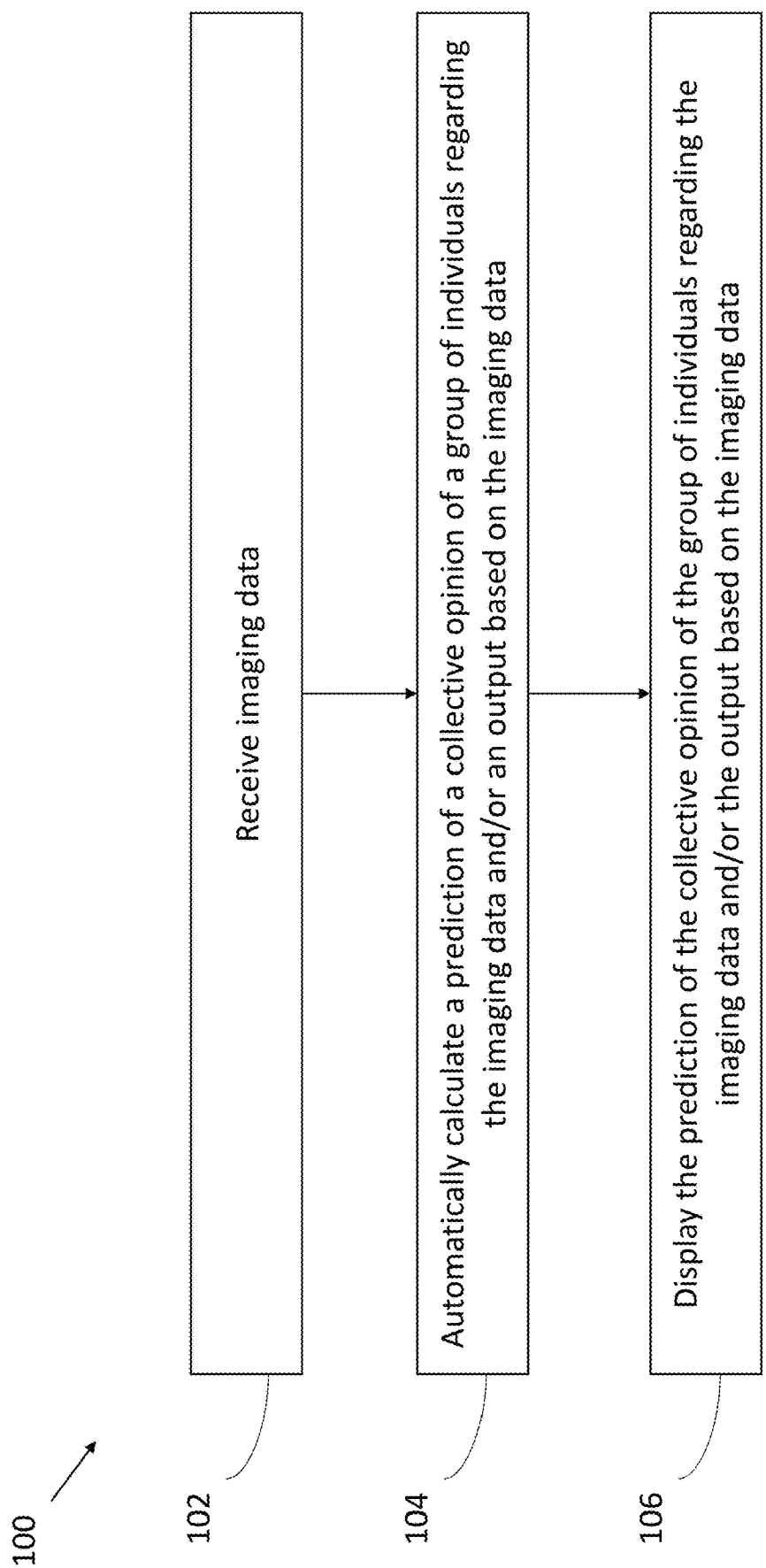
FIG. 1 illustrates an example process for analyzing imaging data, in accordance with certain embodiments described herein.
Figure 2:
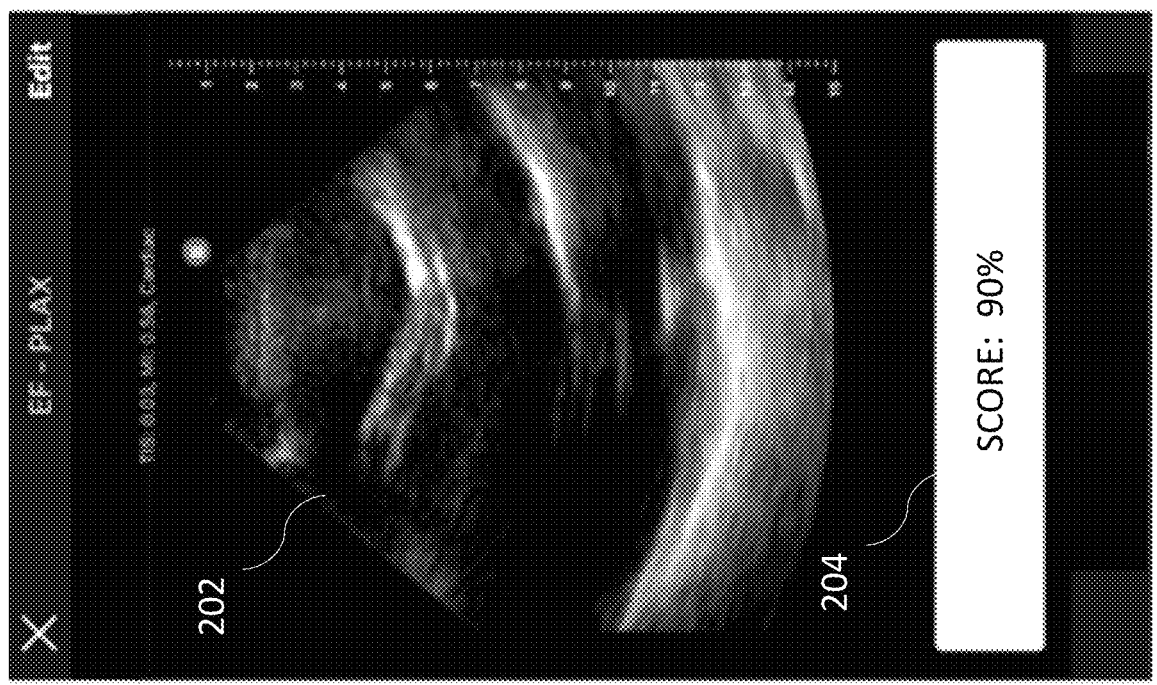
FIG. 2 illustrates an example graphical user interface (GUI), in accordance with certain embodiments described herein.
Figure 3:
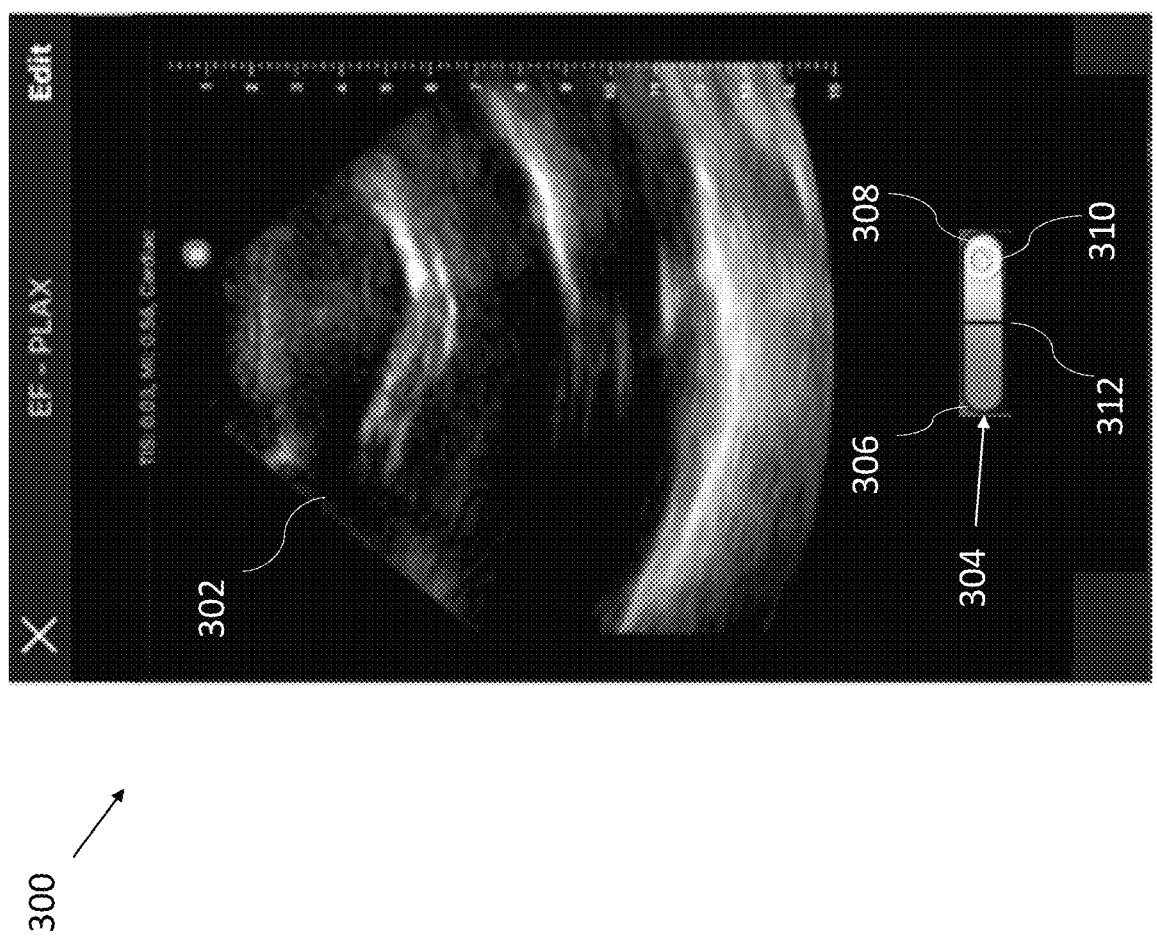
FIG. 3 illustrates another example GUI, in accordance with certain embodiments described herein.
Figure 4:
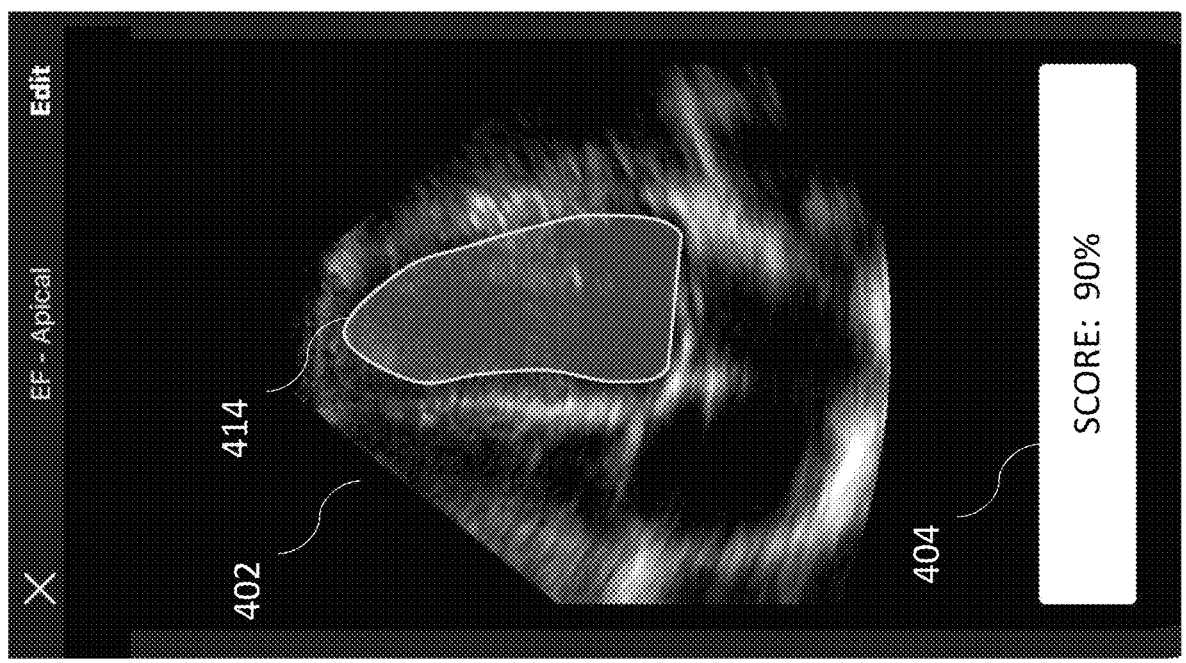
FIG. 4 illustrates another example GUI, in accordance with certain embodiments described herein.
Figure 5:
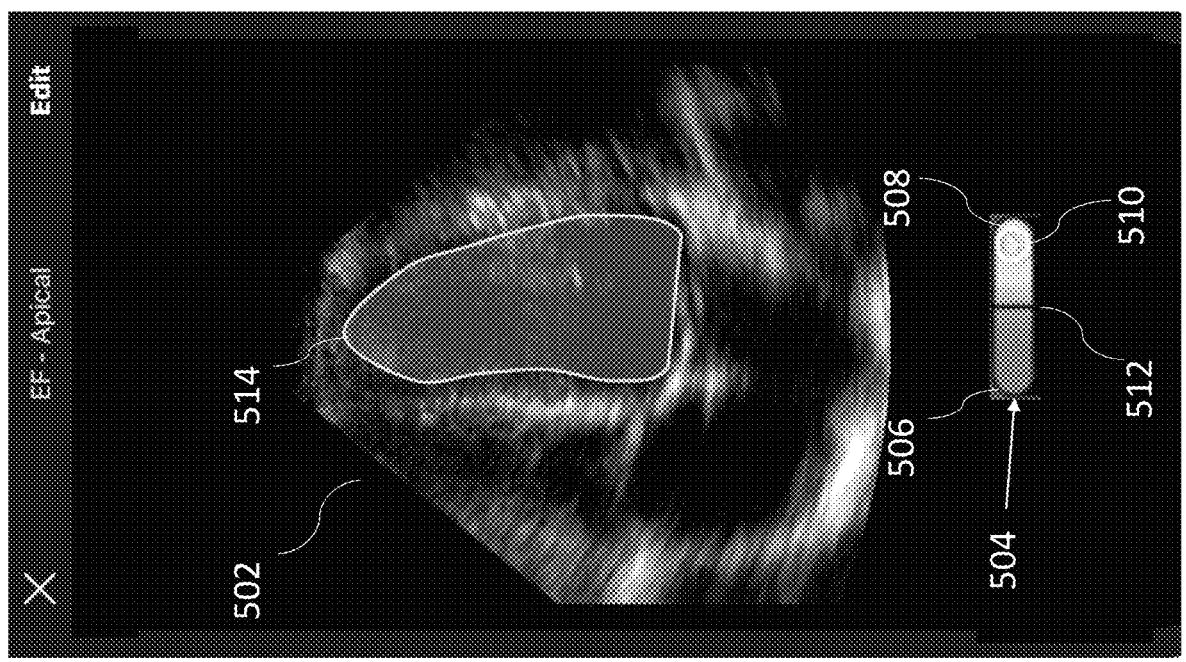
FIG. 5 illustrates another example GUI, in accordance with certain embodiments described herein.

Conventional ultrasound systems are large, complex, and expensive systems that are typically only purchased by large medical facilities with significant financial resources. Recently, cheaper and less complex ultrasound imaging devices have been introduced. Such imaging devices may include ultrasonic transducers and ultrasound processing units (UPUs) monolithically integrated onto a single semiconductor die to form a monolithic ultrasound device. Each UPU may include, for example, high-voltage pulsers to drive the ultrasonic transducers to emit ultrasound waves; analog and mixed-signal receiver channels to receive and digitize ultrasound echoes; digital processing circuitry to filter, compress, and/or beamform the digital data from each channel; and digital sequencing circuit to control and synchronize different parts of the circuitry. An ultrasound-on-chip can form the core of a handheld ultrasound probe or an ultrasound device having another form factor. Aspects of such ultrasound-on-a chip devices are described in U.S. patent application Ser. No. 15/415,434 titled "UNIVERSAL ULTRASOUND DEVICE AND RELATED APPARATUS AND METHODS," filed on Jan. 25, 2017 (and assigned to the assignee of the instant application) and published as U.S. Pat. Pub. 2017/0360397 A1, which is incorporated by reference herein in its entirety. The reduced cost and increased portability of these new ultrasound devices may make them significantly more accessible to the general public than conventional ultrasound devices. At the same time, advances in artificial intelligence technology have enabled performance of automatic measurements on ultrasound images, potentially obviating the need for operators to have the required knowledge for manually performing such measurements. Aspects of such automatic measurements are described in U.S. patent application Ser. No. 15/626,423 titled "AUTOMATIC IMAGE ACQUISITION FOR ASSISTING A USER TO OPERATE AN ULTRASOUND IMAGING DEVICE," filed on Jun. 19, 2017 (and assigned to the assignee of the instant application) and published as U.S. Pat. Pub. 2017/0360401 A1, which is incorporated by reference herein in its entirety.

However, the inventors have recognized that people in the general populace who could make use of such devices have little to no training for how to interpret medical images. The inventors have recognized that it may be helpful for a processing device (which may be in operative communication with an imaging device) to calculate and display, based on collected medical images, metrics that have easily interpretable meanings. The metrics may include a prediction of the collective opinion of a group of individuals (a.k.a., the "wisdom of the crowd") regarding the imaging data and/or regarding an output based on the imaging data.

In terms of predictions of collective opinions regarding imaging data, in some embodiments, a metric may include a prediction of the fraction of the group of individuals who would classify imaging data as clinically usable. For example, if the imaging data is one or more ultrasound images of the heart, the prediction may be a prediction of a fraction of a group of medical professionals skilled in interpreting ultrasound images who would classify the ultrasound images as clinically usable for calculating ejection fraction. In this example, a score of 90% may be interpreted as predicting that 90% of a group of medical professionals skilled in interpreting ultrasound images who classify particular ultrasound images as clinically usable for calculating ejection fraction.

In terms of predictions of collective opinions regarding outputs of imaging data, in some embodiments, a metric may include a prediction of the fraction of a group of individuals who would agree that a segmentation automatically performed based on one or more images was performed correctly. For example, if the imaging data includes an ultrasound image of the heart, the segmentation may include segmenting (i.e., defining which pixels of the ultrasound image include) the left ventricle of the heart from the rest of the image, and the prediction may be a prediction of the fraction of a group of medical professionals skilled in interpreting ultrasound images who would agree that the segmentation of the left ventricle was performed correctly. In this example, a score of 90% may be interpreted as predicting that 90% of a group of medical professionals skilled in interpreting ultrasound images who classify agree that a particular segmentation of a left ventricle in a particular ultrasound images was performed correctly.

In some embodiments, the prediction may include a segmentation mask, where the value of some property (e.g., transparency, brightness, color) of each pixel in the segmentation mask may be proportional to a prediction of the fraction of a group of individuals who would believe the corresponding pixel in the original image is inside a segmented region. Using the left ventricle segmentation example of above, the prediction may be a segmentation mask where the transparency of each pixel in the segmentation mask is proportional to the fraction of a group of medical professionals skilled in interpreting ultrasound images who would believe the corresponding pixel in the ultrasound image is within the left ventricle. In some embodiments, the segmentation mask may be overlaid on the original image In some embodiments, a metric may include a prediction of a distribution or an approximation of a distribution of measurement values that would be manually calculated based on the imaging data by the group of individuals. For example, if the imaging data is one or more ultrasound images of the heart, the prediction may be a prediction of the distribution of ejection fraction values, or the prediction may be a prediction of the mean, standard deviation, confidence interval, or percentile of the ejection fraction values that would be manually calculated from the ultrasound images by a group of medical professionals skilled in interpreting ultrasound images. In this example, a distribution having a mean of 60 and a standard deviation of 10 may be interpreted as predicting that if each individual of a group of medical professionals skilled in interpreting ultrasound images were to manually calculate an ejection fraction value based on ultrasound images, the mean value of the all the ejection values would be 60 and the standard deviation among all the ejection fraction values would be 10. The inventors have recognized that a statistical model may be used to calculate and display such metrics.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

FIG. 1 illustrates an example process 100 for analyzing imaging data, in accordance with certain embodiments described herein. The process 100 is performed by a processing device. The processing device may be, for example, a mobile phone, tablet, or laptop.

In act 102, the processing device receives imaging data (e.g., ultrasound data). In some embodiments, the processing device may receive the imaging data from an imaging device that collected the imaging data. The processing device may be in operative communication with the imaging device that collected the imaging data. As an example, the processing device may receive ultrasound data from an ultrasound device. In some embodiments, the ultrasound device may collect raw acoustical data, transmit the raw acoustical data to the processing device, and the processing device may generate an ultrasound image from the raw acoustical data. In some embodiments, the ultrasound device may collect raw acoustical data, generate an ultrasound image from the raw acoustical data, and transmit the ultrasound image to the processing device. In some embodiments, the ultrasound device may collect raw acoustical data, generate scan lines from the raw acoustical data, transmit the scan lines to the processing device, and the processing device may generate an ultrasound image from the scan lines. In some embodiments, the processing device may receive the imaging data from another processing device (which may, in turn, have received the imaging data from an imaging device). The process 100 proceeds from act 102 to act 104.

In act 104, the processing device automatically calculates a prediction of a collective opinion of a group of individuals regarding imaging data and/or regarding an output based on the imaging data. In some embodiments, the processing device may automatically calculate the prediction in real-time, as the imaging data is collected. For example, the processing device may receive imaging data from an imaging device after the imaging data is collected, and upon receiving the imaging data, automatically calculate the prediction.

In terms of predictions of collective opinions regarding imaging data, in some embodiments, the prediction may be a prediction of the collective opinion of a group of individuals regarding the usability of the imaging data. In such embodiments, the prediction may be a prediction of the fraction of a group of individuals who would classify the imaging data as clinically usable. For example, if the imaging data is one or more ultrasound images of the heart, the prediction may be a prediction of the fraction of a group of medical professionals skilled in interpreting ultrasound images who would classify the ultrasound images as clinically usable for calculating ejection fraction.

In terms of predictions of collective opinions regarding outputs based on imaging data, in some embodiments, the prediction may be a prediction of the collective opinion of a group of individuals regarding a segmentation of the imaging data. In some embodiments, the processing device may automatically perform a segmentation based on imaging data (e.g., on one or more ultrasound images). In some embodiments, a user may use the processing device to perform a segmentation based imaging data. In some embodiments, the processing device may automatically perform a segmentation and the user may modify the segmentation. The segmentation may include, for example, defining which pixels of an image are part of one feature and which pixels of the image are not part of that feature. In some embodiments, the prediction may be a prediction of the fraction of a group of individuals who would agree that the segmentation was performed correctly. For example, if the imaging data includes an ultrasound image of the heart, the segmentation may include segmenting (i.e., defining which pixels of the ultrasound image include) the left ventricle of the heart from the rest of the image, and the prediction may be a prediction of the fraction of a group of medical professionals skilled in interpreting ultrasound images who would agree that the segmentation of the left ventricle was performed correctly.

In some embodiments, the prediction may be a prediction of the fraction of a group of individuals who would believe that a given pixel in the original image is within the segmented region. In some embodiments, calculating the prediction may include generating a segmentation mask where the value of some property (e.g., brightness, transparency, color) of each pixel in the segmentation mask is proportional to a prediction of the fraction of a group of individuals who would believe the corresponding pixel in the original image is inside a segmented region. For example, the segmentation mask and the original image may be the same size (in pixels), and corresponding pixels may be pixels at the same location in each image. Using the left ventricle segmentation example of above, the prediction may be a segmentation mask where the transparency of each pixel in the segmentation image is proportional to a prediction of the fraction of a group of medical professionals skilled in interpreting ultrasound images who would believe the corresponding pixel in the ultrasound image is within the left ventricle. In some embodiments, the segmentation mask may be overlaid on the original image.

In some embodiments, the prediction may be a prediction of the collective opinion of the group of individuals regarding a measurement performed based on the imaging data. In some embodiments, the prediction may include a prediction of the distribution of measurement values that would be manually calculated based on the imaging data by the group of individuals. In some embodiments, the prediction may be a prediction of an approximation of such a distribution, such as a mean, a standard deviation, a confidence interval, or a percentile of a distribution of measurement values. For example, if the imaging data is one or more ultrasound images of the heart, the prediction may be a prediction of the distribution of ejection fraction values and/or the mean and standard deviation of the distribution of ejection fraction values that would be manually calculated based on the ultrasound images by a group of medical professionals skilled in interpreting ultrasound images.

In some embodiments, to automatically calculate the prediction of the collective opinion of the group of individuals regarding imaging data, the processing device may use a statistical model. The statistical model may be stored on the processing device, or may be stored on another processing device (e.g., a server) and the processing device may access the statistical model on that other processing device. The statistical model may be trained on multiple sets of imaging data (e.g., each set may include one or more ultrasound images), each set of imaging data labeled with the collective opinion of a group of individuals regarding the imaging data. Based on the training, the statistical model may learn to calculate a prediction of a collective opinion of the group of individuals regarding new imaging data. The more training data used, the closer the prediction may come to predicting the collective opinion of an infinite group of individuals regarding new imaging data.

In embodiments in which the prediction includes a prediction of the fraction of a group of individuals who would classify the imaging data as clinically usable, the statistical model may be trained on multiple sets of imaging data, each set of training imaging data labeled with the fraction of the group of individuals who would classify the imaging data as clinically usable. For example, if each set of training imaging data includes one or more ultrasound images of the heart, each set may be labeled with the fraction of a group of medical professionals skilled in interpreting ultrasound images who would classify the ultrasound images as clinically usable for calculating ejection fraction. To collect this training data, each set of ultrasound images may be shown to multiple medical professionals, each medical professional may classify the set of ultrasound images as clinically usable for calculating ejection fraction, and the fraction of the medical professionals who classified each set of ultrasound images as clinically usable for calculating ejection fraction may be calculated. Based on the training, the statistical model may learn to calculate a prediction of the fraction of the group of medical professionals skilled in interpreting ultrasound images who would classify a new set of ultrasound images as clinically usable for calculating ejection fraction.

In embodiments in which the prediction includes a prediction of the fraction of the group of individuals who would agree that a segmentation performed based on the imaging data was performed correctly, the statistical model may be trained on multiple sets of training imaging data with segmentations performed based on them, each set of training imaging data labeled with the fraction of the group of individuals who would agree that a segmentation performed based on the imaging data was performed correctly. For example, if each set of training imaging data includes an ultrasound image of the heart, where the left ventricle in each image has been segmented (automatically or manually or a combination of automatically and manually), each set may be labeled with the fraction of a group of medical professionals skilled in interpreting ultrasound images who would agree that the segmentation was performed correctly. To collect this training data, each ultrasound image and the segmentation may be shown to multiple medical professionals, each medical professional may determine whether s/he agrees with the segmentation, and the fraction of the medical professionals who agreed with the segmentation may be calculated. Based on the training, the statistical model may learn to calculate a prediction of the fraction of the group of medical professionals skilled in interpreting ultrasound images who would agree that a new left ventricle segmentation performed based on a new ultrasound image was performed correctly.

In embodiments in which the prediction includes a prediction of the fraction of a group of individuals who would believe that a given pixel in the original image is within the segmented region, the statistical model may be trained on multiple sets of imaging data, each set of training imaging data associated with a segmentation mask. This segmentation mask may be the same size as the original image, and the value of some property (e.g., transparency, brightness, color) of each pixel in the segmentation mask may be proportional to a prediction of the fraction of a group of individuals who would believe the corresponding pixel in the original image is inside a segmented region. For example, if each set of training imaging data includes an ultrasound image of the heart, the ultrasound image in each set may be associated with a segmentation mask that is the same size as the ultrasound image, and the transparency of each pixel in the segmentation mask may be proportional to a prediction of the fraction of a group of medical professionals skilled in interpreting ultrasound images who would believe the corresponding pixel in the ultrasound image is within the left ventricle. To collect this training data, each medical professional may produce a segmentation mask for each ultrasound image, where the segmentation mask is the same size (in pixels) as the ultrasound image, and pixels in the segmentation mask that the particular medical professional believes are within the segmented region may be labeled with a 1, and pixels in the segmentation mask that the particular medical professional believes are outside the segmented region may be labeled with a 0. Then, all the medical professionals' segmentation masks for a given ultrasound image may be averaged together to produce a final segmentation mask where the transparency of each pixel in the final segmentation mask is proportional to the average value of that pixel from among all the individual segmentation masks. For example, if half of all the medical professionals labeled a pixel as 1 (i.e., within the segmented region) and half of all the medical professionals labeled a pixel as 0 (i.e., outside the segmented region), then the transparency of that pixel in the final segmentation mask may be proportional to 0.5. This final segmentation mask may then be associated with the ultrasound image in the training data set. Based on the training, the statistical model may learn to generate a left ventricle segmentation mask where the transparency value of each pixel in the segmentation image may be proportional to a prediction of the fraction of a group of medical professionals skilled in interpreting ultrasound images who would believe the corresponding pixel in the original image is inside the left ventricle. In embodiments in which the value of each pixel in the segmentation image may be proportional to a prediction of the fraction of a group of individuals who would believe the corresponding pixel in the original image is outside a segmented region, collection of training data may be the same as described above, but pixels in the mask image that the particular medical professional believes are within the segmented region may be labeled with a 0, and pixels in the mask image that the particular medical professional believes are outside the segmented region may be labeled with a 1.

In embodiments in which the prediction includes a prediction of a distribution or an approximation (e.g., mean, standard deviation, confidence interval, percentile) of a distribution of measurement values that would be manually calculated based on the imaging data by the group of, each set of imaging data may be labeled with the distribution or an approximation of a distribution of measurement values manually calculated based on the imaging data by the group of individuals. For example, if each set of imaging data includes one or more ultrasound images of the heart, each set may be labeled with the manually calculated measurement values. As another example, each set may be labeled with the mean and/or standard deviation of the manually calculated measurements. To collect this training data, each set of ultrasound images may be shown to multiple medical professionals and each medical professional may measure an ejection fraction value based on the ultrasound images. The mean and/or deviation of all the ejection fraction values may also be calculated. Based on the training, the statistical model may learn to calculate a prediction of the distribution and/or an approximation a distribution of ejection fraction values that would be manually calculated based on the ultrasound images by the group of medical professionals skilled in interpreting ultrasound images. The process 100 proceeds from act 104 to act 106.

In act 106, the processing device displays the prediction of the collective opinion of the group of individuals regarding the imaging data and/or the output based on the imaging data that was calculated in act 104. In embodiments in which the processing device automatically calculates the prediction in real-time, as the imaging data is collected, the processing device may also display the prediction in real-time. For example, the processing device may receive imaging data from an imaging device after the imaging data is collected, and upon receiving the imaging data, automatically calculate and display the prediction.

In some embodiments, displaying the prediction may include displaying a fraction as a number (e.g., in fractional, decimal, or percentage form). In some embodiments, displaying the prediction may include displaying a frame having a first end and a second end and a marker within the frame. The distance from the first end of the frame to the marker divided by the distance from the first end to the second of the marker may be approximately equal to a fraction. In some embodiments, the displayed fraction may be the predicted fraction of the group of individuals who would classify the imaging data as clinically usable. In some embodiments, the displayed fraction may be the predicted fraction of the group of individuals who would agree that a segmentation automatically performed based on one or more images was performed correctly.

In some embodiments, displaying the prediction may include displaying a segmentation mask. In some embodiments, the segmentation image may be such that the value of some property (e.g., brightness, transparency, color) of each pixel in the segmentation image is proportional to a prediction of the fraction of a group of individuals who would believe the corresponding pixel in the original image is inside a segmented region. In some embodiments, the segmentation image may be overlaid on the original image.

In some embodiments, displaying the prediction may include graphically displaying a distribution. In some embodiments, displaying the prediction may include displaying an approximation (e.g., mean, standard deviation, confidence interval, percentile) as a number or numbers. In some embodiments, the distribution may be a prediction of the distribution, or an approximation of the distribution, of measurement values that would be manually calculated based on the imaging data by the group of individuals.

In some embodiments, the processing device may display the prediction with the imaging data. For example, if the imaging data is one or more ultrasound images, the processing device may display the prediction adjacent to or superimposed on one or more of the ultrasound images. If the imaging data includes one or more ultrasound images on which segmentations have been performed, the processing device may display the prediction adjacent to or superimposed on one or more of the ultrasound images, where the segmentation is displayed on or more of the ultrasound images. The segmentation may include a mask where some pixels (corresponding to those within the segmented region) are opaque or semi-opaque and some pixels (corresponding to those outside the segmented region) are transparent, or as an outline of the boundary between pixels within and outside the segmented region.

In some embodiments, act 104 may be absent. For example, the processing device may receive the prediction from another device and then display it. In some embodiments, act 102 may be absent. Again, for example, the processing device may receive the prediction from another device and then display it. In some embodiments, act 106 may be absent. For example, the processing device may calculate the prediction but not display it. Rather, the processing device may transmit the prediction to another device for display.

FIGS. 2-8 illustrate examples of graphical user interfaces (GUIs) 200-800, respectively, in accordance with certain embodiments described herein. The GUIs may be displayed by a processing device. The processing device may be, for example, a mobile phone, tablet, or laptop. In some embodiments, the processing device may be in operative communication with an imaging device (e.g., an ultrasound device) that collects imaging data (e.g., ultrasound data).

The GUI 200 includes an ultrasound image 202 and a prediction 204. The ultrasound image 202 is a one of a series of ultrasound images collected over a time period. The prediction 204 is a prediction of the fraction (i.e., 90%) of a group of medical professionals skilled in interpreting ultrasound images who would classify the series of the ultrasound images from which the ultrasound image 202 is a part as clinically usable for calculating ejection fraction.

The GUI 300 includes an ultrasound image 302, a bar 304 having a first end 306 and a second end 308, a marker 310, and a threshold indicator 312. The ultrasound image 302 is a one of a series of ultrasound images collected over a time period. The ratio of the distance between the first end 306 and the marker 310 along the bar 304 to the distance between the first end 306 and the second end 308 along the bar 304 is equivalent to a fraction. In particular, this fraction is a prediction of the fraction of a group of medical professionals skilled in interpreting ultrasound images who would classify the series of the ultrasound images from which the ultrasound image 302 is a part as clinically usable for calculating ejection fraction. The threshold indicator 312 is located 50% of the distance along the bar 304 from the first end 306 to the second end 308. This may help a user to gauge how far along the bar 304 the marker 310 is, by comparing the location of the marker 310 to the location of the threshold indicator 312. Additionally, the processing device displays a checkmark symbol in the marker 310 when the marker 310 is between the threshold indicator 310 and the second end 308, and displays an "x" symbol in the marker 310 when the marker 310 is between the first end. In some embodiments, the threshold indicator 312 may be absent. In some embodiments, the processing device may not display a checkmark symbol or an "x" symbol.

The GUI 400 includes an ultrasound image 402, a segmentation 414, and a prediction 404. The segmentation 414 segments the left ventricle of the heart in the ultrasound image 402 from the rest of the ultrasound image 402. The prediction 404 is a prediction of the fraction (i.e., 90%) of a group of medical professionals skilled in interpreting ultrasound images who would agree that the segmentation 414 of the left ventricle was performed correctly.

The GUI 500 includes an ultrasound image 502, a segmentation 514, a bar 504 having a first end 506 and a second end 508, a marker 510, and a threshold indicator 512. The segmentation 514 segments the left ventricle of the heart in the ultrasound image 502 from the rest of the ultrasound image 502. The ratio of the distance between the first end 506 and the marker 510 along the bar 504 to the distance between the first end 506 and the second end 508 along the bar 504 is equivalent to a fraction. In particular, this fraction is a prediction of the fraction of a group of medical professionals skilled in interpreting ultrasound images who would agree that the segmentation 514 of the left ventricle was performed correctly. The threshold indicator 512 is located 50% of the distance along the bar 504 from the first end 506 to the second end 508. This may help a user to gauge how far along the bar 504 the marker 510 is, by comparing the location of the marker 510 to the location of the threshold indicator 512. Additionally, the processing device displays a checkmark symbol in the marker 510 when the marker 510 is between the threshold indicator 510 and the second end 508, and displays an "x" symbol in the marker 510 when the marker 510 is between the first end 506 and the threshold indicator 510. In some embodiments, the threshold indicator 512 may be absent. In some embodiments, the processing device may not display a checkmark symbol or an "x" symbol.

Figure 6:
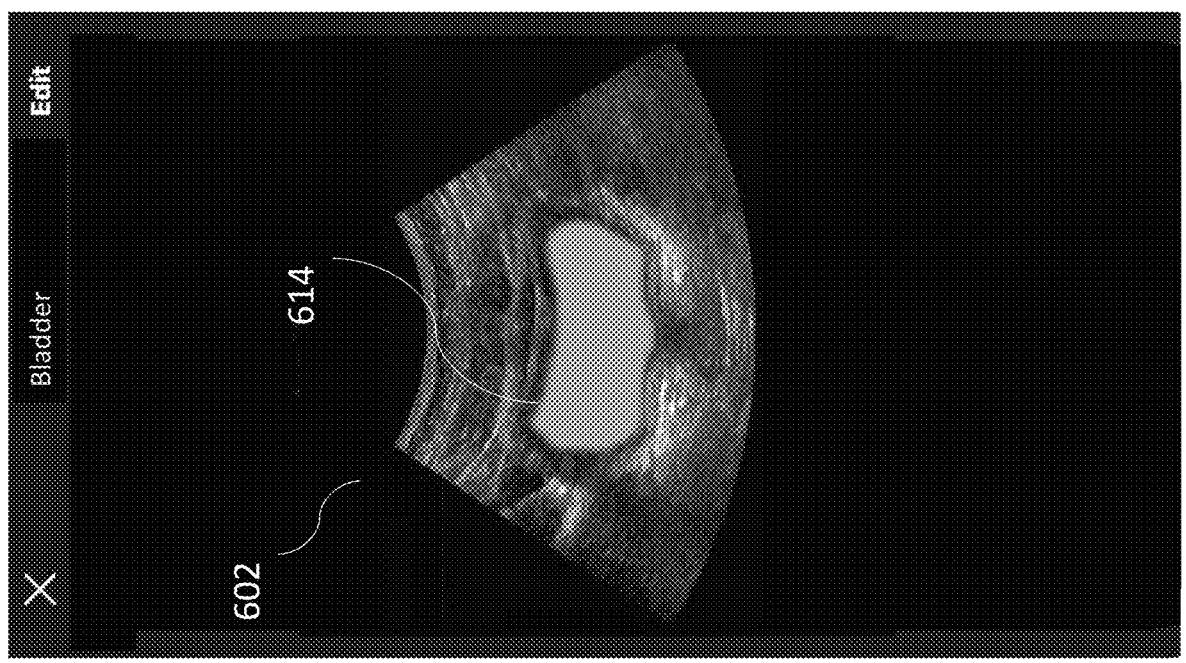
FIG. 6 illustrates another example GUI, in accordance with certain embodiments described herein.
Figure 7:
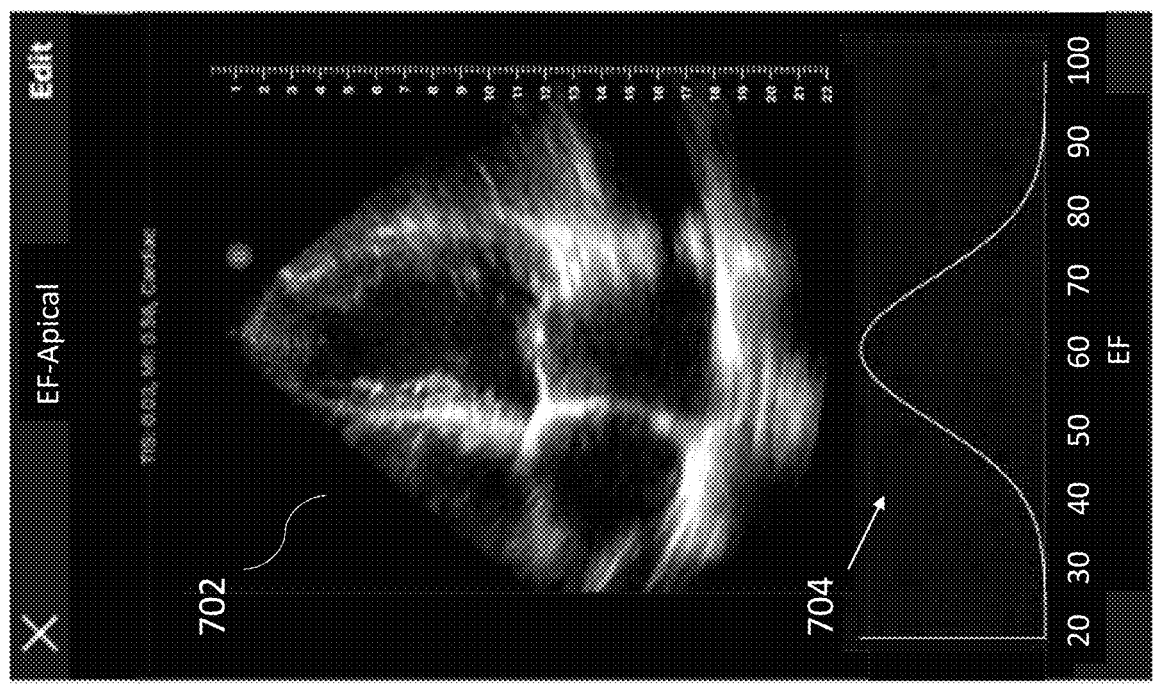
FIG. 7 illustrates another example GUI, in accordance with certain embodiments described herein.
Figure 8:
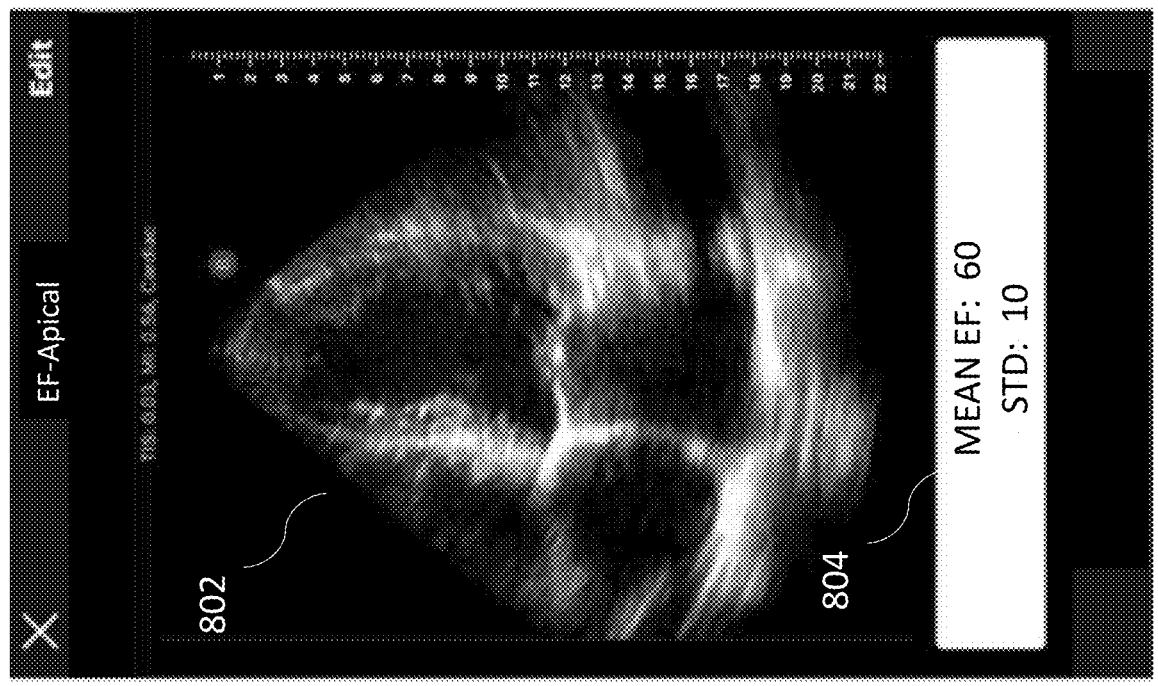
FIG. 8 illustrates another example GUI, in accordance with certain embodiments described herein.

The GUI 600 includes an ultrasound image 602 and a segmentation mask 614. The transparency of each pixel in the segmentation mask 614 may be proportional to a prediction of the fraction of a group of medical professional skilled in interpreting ultrasound images who would believe the corresponding pixel in the ultrasound image 602 is within the bladder depicted in the ultrasound image 602. In FIG. 6, the segmentation mask 614 depicts a region having an opaque center (corresponding to a large fraction of medical professionals who would believe those pixels are within the bladder) and more transparent edges (corresponding to a smaller fraction of medical professionals who would believe those pixels are within the bladder).

The GUI 700 includes an ultrasound image 702 and a graph of a distribution 704. The ultrasound image 702 is a one of a series of ultrasound images collected over a time period. The graph of the distribution 704 shows a prediction of a distribution of ejection fraction values that would be manually calculated based on the series of ultrasound images of which the ultrasound image 702 is a part by a group of medical professionals skilled in interpreting ultrasound images.

The GUI 800 includes an ultrasound image 802 and a prediction 804. The ultrasound image 802 is a one of a series of ultrasound images collected over a time period. The prediction 804 includes a prediction of a mean (i.e., 60 (in units of percent points)) and standard deviation (i.e., 10 (in units of percent points)) among ejection fraction values that would be manually calculated based on the series of ultrasound images of which the ultrasound image 802 is a part by a group of medical professionals skilled in interpreting ultrasound images. In some embodiments, the processing device may display other approximations of distributions, such as confidence intervals or percentiles.

It should be appreciated that the forms of the GUIs 300-800 are not limiting, and alternative forms that still display the described predictions may be used. For example, the layouts, shapes, colors, texts, may vary.

Figure 9:
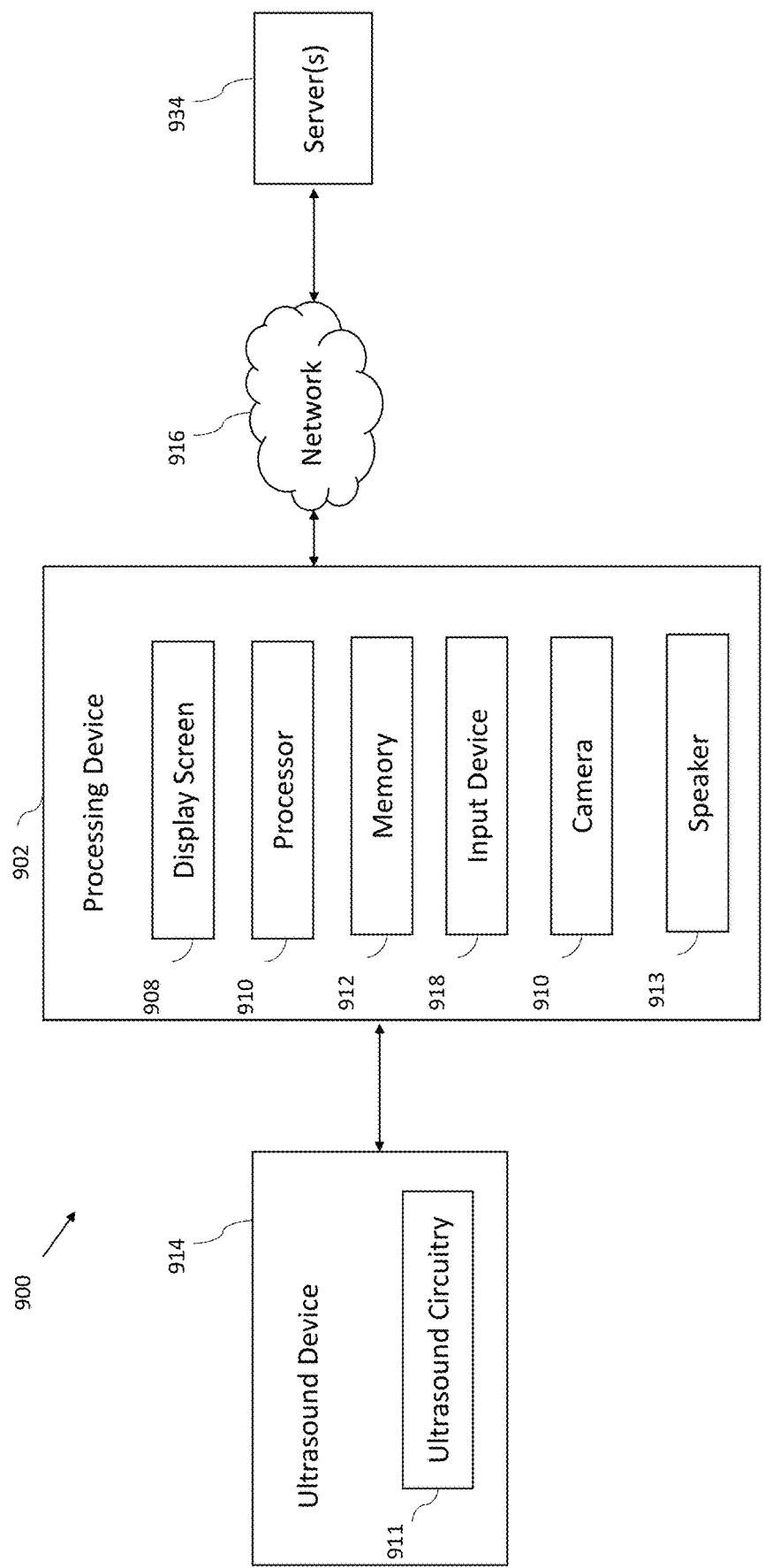
FIG. 9 illustrates a schematic block diagram of an example ultrasound system upon which various aspects of the technology described herein may be practiced.

FIG. 9 illustrates a schematic block diagram of an example ultrasound system 900 upon which various aspects of the technology described herein may be practiced. The ultrasound system 900 includes an ultrasound device 914, a processing device 902, a network 916, and one or more servers 934.

The ultrasound device 914 includes ultrasound circuitry 911. The processing device 902 includes a camera 910, a display screen 908, a processor 910, a memory 912, an input device 918, and a speaker 913. The processing device 902 is in wired (e.g., through a lightning connector or a mini-USB connector) and/or wireless communication (e.g., using BLUETOOTH, ZIGBEE, and/or WiFi wireless protocols) with the ultrasound device 914. The processing device 902 is in wireless communication with the one or more servers 934 over the network 916. However, the wireless communication with the processing device 934 is optional.

The ultrasound device 914 may be configured to generate ultrasound data that may be employed to generate an ultrasound image. The ultrasound device 914 may be constructed in any of a variety of ways. In some embodiments, the ultrasound device 914 includes a transmitter that transmits a signal to a transmit beamformer which in turn drives transducer elements within a transducer array to emit pulsed ultrasonic signals into a structure, such as a patient. The pulsed ultrasonic signals may be back-scattered from structures in the body, such as blood cells or muscular tissue, to produce echoes that return to the transducer elements. These echoes may then be converted into electrical signals by the transducer elements and the electrical signals are received by a receiver. The electrical signals representing the received echoes are sent to a receive beamformer that outputs ultrasound data. The ultrasound circuitry 911 may be configured to generate the ultrasound data. The ultrasound circuitry 911 may include one or more ultrasonic transducers monolithically integrated onto a single semiconductor die. The ultrasonic transducers may include, for example, one or more capacitive micromachined ultrasonic transducers (CMUTs), one or more CMOS (complementary metal-oxide-semiconductor) ultrasonic transducers (CUTs), one or more piezoelectric micromachined ultrasonic transducers (PMUTs), and/or one or more other suitable ultrasonic transducer cells. In some embodiments, the ultrasonic transducers may be formed the same chip as other electronic components in the ultrasound circuitry 911 (e.g., transmit circuitry, receive circuitry, control circuitry, power management circuitry, and processing circuitry) to form a monolithic ultrasound device. The ultrasound device 914 may transmit ultrasound data and/or ultrasound images to the processing device 902 over a wired (e.g., through a lightning connector or a mini-USB connector) and/or wireless (e.g., using BLUETOOTH, ZIGBEE, and/or WiFi wireless protocols) communication link.

Referring now to the processing device 902, the processor 910 may include specially-programmed and/or special-purpose hardware such as an application-specific integrated circuit (ASIC). For example, the processor 910 may include one or more graphics processing units (GPUs) and/or one or more tensor processing units (TPUs). TPUs may be ASICs specifically designed for machine learning (e.g., deep learning). The TPUs may be employed to, for example, accelerate the inference phase of a neural network. The processing device 902 may be configured to process the ultrasound data received from the ultrasound device 914 to generate ultrasound images for display on the display screen 908. The processing may be performed by, for example, the processor 910. The processor 910 may also be adapted to control the acquisition of ultrasound data with the ultrasound device 914. The ultrasound data may be processed in real-time during a scanning session as the echo signals are received. In some embodiments, the displayed ultrasound image may be updated a rate of at least 5 Hz, at least 10 Hz, at least 20 Hz, at a rate between 5 and 60 Hz, at a rate of more than 20 Hz. For example, ultrasound data may be acquired even as images are being generated based on previously acquired data and while a live ultrasound image is being displayed. As additional ultrasound data is acquired, additional frames or images generated from more-recently acquired ultrasound data are sequentially displayed. Additionally, or alternatively, the ultrasound data may be stored temporarily in a buffer during a scanning session and processed in less than real-time.

The processing device 902 may be configured to perform certain of the processes described herein using the processor 910 (e.g., one or more computer hardware processors) and one or more articles of manufacture that include non-transitory computer-readable storage media such as the memory 912. The processor 910 may control writing data to and reading data from the memory 912 in any suitable manner. To perform certain of the processes described herein, the processor 910 may execute one or more processor-executable instructions stored in one or more non-transitory computer-readable storage media (e.g., the memory 912), which may serve as non-transitory computer-readable storage media storing processor-executable instructions for execution by the processor 910. The camera 910 may be configured to detect light (e.g., visible light) to form an image. The camera 910 may be on the same face of the processing device 902 as the display screen 908. The display screen 908 may be configured to display images and/or videos, and may be, for example, a liquid crystal display (LCD), a plasma display, and/or an organic light emitting diode (OLED) display on the processing device 902. The input device 918 may include one or more devices capable of receiving input from a user and transmitting the input to the processor 910. For example, the input device 918 may include a keyboard, a mouse, a microphone, touch-enabled sensors on the display screen 908, and/or a microphone. The display screen 908, the input device 918, the camera 910, and the speaker 913 may be communicatively coupled to the processor 910 and/or under the control of the processor 910.

It should be appreciated that the processing device 902 may be implemented in any of a variety of ways. For example, the processing device 902 may be implemented as a handheld device such as a mobile smartphone or a tablet. Thereby, a user of the ultrasound device 914 may be able to operate the ultrasound device 914 with one hand and hold the processing device 902 with another hand. In other examples, the processing device 902 may be implemented as a portable device that is not a handheld device, such as a laptop. In yet other examples, the processing device 902 may be implemented as a stationary device such as a desktop computer. The processing device 902 may be connected to the network 916 over a wired connection (e.g., via an Ethernet cable) and/or a wireless connection (e.g., over a WiFi network). The processing device 902 may thereby communicate with (e.g., transmit data to) the one or more servers 934 over the network 916. For further description of ultrasound devices and systems, see U.S. patent application Ser. No. 15/415,434 titled "UNIVERSAL ULTRASOUND DEVICE AND RELATED APPARATUS AND METHODS," filed on Jan. 25, 2017 and published as U.S. Pat. App. Publication No. 2017-0360397 A1 (and assigned to the assignee of the instant application).

FIG. 9 should be understood to be non-limiting. For example, the ultrasound system 900 may include fewer or more components than shown and the processing device 902 may include fewer or more components than shown.

While the above description has focused on ultrasound imaging data and ultrasound devices, it should be appreciated that the same concepts may be applied to other types of imaging data and devices, such as X-ray, computed tomography (CT), magnetic resonance imaging (MRI).

Various inventive concepts may be embodied as one or more processes, of which examples have been provided. The acts performed as part of each process may be ordered in any suitable way. Thus, embodiments may be constructed in which acts are performed in an order different than illustrated, which may include performing some acts simultaneously, even though shown as sequential acts in illustrative embodiments. Further, one or more of the processes may be combined and/or omitted, and one or more of the processes may include additional steps.

Various aspects of the present disclosure may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. An apparatus, comprising:
processing circuitry communicatively coupled to an ultrasound imaging device and configured to:
receive ultrasound imaging data from the ultrasound imaging device;
automatically calculate a prediction of a collective opinion of a group of individuals regarding: (a) the ultrasound imaging data; and/or (b) an output based on the ultrasound imaging data, by electronically processing the ultrasound imaging data and/or the output based on the ultrasound imaging data using a statistical model, wherein the processing circuitry is configured, when automatically calculating the prediction of the collective opinion of the group of individuals regarding: (a) the ultrasound imaging data; and/or (b) the output based on the ultrasound imaging data, to calculate a prediction of a fraction of the group of individuals who would classify the ultrasound imaging data as clinically usable; and
display, simultaneously via a graphical user interface (GUI), the ultrasound imaging data with a visual indicator indicative of the prediction, wherein:
the processing circuitry is configured to automatically calculate the prediction and display the visual indicator indicative of the prediction in real-time as the ultrasound imaging data is collected; and
the processing circuitry is configured, when displaying the visual indicator indicative of the prediction, to display:
a frame having a first end and a second end; and
a marker within the frame;
such that a distance from the first end of the frame to the marker divided by the distance from the first end of the frame to the second end of the frame is approximately equal to the fraction.

2. The apparatus of claim 1, wherein the processing circuitry is configured, when automatically calculating the prediction of the collective opinion of the group of individuals regarding: (a) the ultrasound imaging data; and/or (b) the output based on the ultrasound imaging data, to calculate a prediction of a collective opinion of a group of individuals regarding usability of ultrasound imaging data.

3. The apparatus of claim 1, wherein the processing circuitry is configured, when displaying the visual indicator indicative of the prediction, to display the fraction.

4. The apparatus of claim 1, wherein the processing circuitry is configured, when automatically calculating the prediction of the collective opinion of the group of individuals regarding: (a) the ultrasound imaging data; and/or (b) the output based on the ultrasound imaging data, to calculate a prediction of a collective opinion of a group of individuals regarding a segmentation of the ultrasound imaging data.

5. The apparatus of claim 1, wherein the processing circuitry is configured, when automatically calculating the prediction of the collective opinion of the group of individuals regarding: (a) the ultrasound imaging data; and/or (b) the output based on the ultrasound imaging data, to calculate a prediction of a fraction of the group of individuals who would agree that a segmentation automatically performed based on one or more images was performed correctly.

6. The apparatus of claim 5, wherein the processing circuitry is configured, when displaying the visual indicator indicative of the prediction, to display the fraction.

7. The apparatus of claim 5, wherein the processing circuitry is configured, when displaying the visual indicator indicative of the prediction, to display:
a frame having a first end and a second end; and a marker within the frame;
such that a distance from the first end of the frame to the marker divided by the distance from the first end to the second of the marker is approximately equal to the fraction.

8. The apparatus of claim 1, wherein the processing circuitry is configured, when automatically calculating the prediction of the collective opinion of the group of individuals regarding: (a) the ultrasound imaging data; and/or (b) the output based on the ultrasound imaging data, to calculate a prediction of the fraction of a group of individuals who would believe that a given pixel in an image is within a segmented region.

9. The apparatus of claim 1, wherein the processing circuitry is configured, when automatically calculating the prediction of the collective opinion of the group of individuals regarding: (a) the ultrasound imaging data; and/or (b) the output based on the ultrasound imaging data, to generate a segmentation mask where a value of a property of each pixel in the segmentation mask is proportional to a prediction of a fraction of the group of individuals who would believe that a corresponding pixel in an image is inside a segmented region.

10. The apparatus of claim 9, wherein the processing circuitry is configured, when displaying the visual indicator indicative of the prediction, to display the segmentation mask.

11. The apparatus of claim 10, wherein the processing circuitry is configured to overlay the segmentation mask on the image.

12. The apparatus of claim 1, wherein the processing circuitry is configured, when automatically calculating the prediction of the collective opinion of the group of individuals regarding: (a) the ultrasound imaging data; and/or (b) the output based on the ultrasound imaging data, to calculate a prediction of a collective opinion of a group of individuals regarding a measurement performed based on the ultrasound imaging data.

13. The apparatus of claim 1, wherein the processing circuitry is configured, when automatically calculating the prediction of the collective opinion of the group of individuals regarding: (a) the ultrasound imaging data; and/or (b) the output based on the ultrasound imaging data, to calculate a prediction of a distribution of measurement values that would be manually calculated based on the ultrasound imaging data by the group of individuals.

14. The apparatus of claim 13, wherein the processing circuitry is configured, when displaying the visual indicator indicative of the prediction, to graphically display the distribution.

15. The apparatus of claim 1, wherein the processing circuitry is configured, when automatically calculating the prediction of the collective opinion of the group of individuals regarding: (a) the ultrasound imaging data; and/or (b) the output based on the ultrasound imaging data, to predict an approximation of a distribution of measurement values of the ultrasound imaging data that would result from a manual calculation process.

16. The apparatus of claim 15, wherein the approximation comprises a mean, a standard deviation, a confidence interval, and/or a percentile.

17. The apparatus of claim 15, wherein the processing circuitry is configured, when displaying the visual indicator indicative of the prediction, to display the approximation.

18. The apparatus of claim 1, wherein the processing circuitry is contained within a portable device.

19. The apparatus of claim 18, wherein the portable device is a smartphone or a tablet.

* * * * *